(12) United States Patent
Inderbitzi

(10) Patent No.: US 8,672,964 B2
(45) Date of Patent: Mar. 18, 2014

(54) PUNCTURE SEALS FOR CLOSING HOLLOW ORGANS HAVING A PUNCTURE OPENING

(75) Inventor: Rolf Inderbitzi, Widen (CH)

(73) Assignee: Aesculap AG (DE)

( * ) Notice: Subject to any disclaimer, the term of this patent is extended or adjusted under 35 U.S.C. 154(b) by 749 days.

(21) Appl. No.: 12/504,715

(22) Filed: Jul. 17, 2009

(65) Prior Publication Data

US 2010/0016887 A1    Jan. 21, 2010

(30) Foreign Application Priority Data

Jul. 18, 2008 (DE) .......................... 10 2008 034 534

(51) Int. Cl.
*A61B 17/08* (2006.01)

(52) U.S. Cl.
USPC ........................................................ 606/213

(58) Field of Classification Search
USPC ................. 606/151, 213, 215, 216, 217, 220; 411/401, 486, 500
See application file for complete search history.

(56) References Cited

U.S. PATENT DOCUMENTS

| | | | |
|---|---|---|---|
| 4,512,338 A * | 4/1985 | Balko et al. .................... | 606/108 |
| 4,744,364 A | 5/1988 | Kensey | |
| 5,350,399 A | 9/1994 | Erlebacher et al. | |
| 5,441,517 A | 8/1995 | Kensey et al. | |
| 5,527,337 A * | 6/1996 | Stack et al. .................... | 606/198 |
| 5,582,616 A * | 12/1996 | Bolduc et al. ................. | 606/143 |
| 5,593,422 A | 1/1997 | Muijs Van de Moer et al. | |
| 5,620,461 A | 4/1997 | Muijs Van de Moer et al. | |
| 5,916,236 A | 6/1999 | Muijs Van de Moer et al. | |
| 6,007,562 A | 12/1999 | Harren et al. | |
| 6,113,611 A * | 9/2000 | Allen et al. .................... | 606/151 |
| 6,355,052 B1 * | 3/2002 | Neuss et al. ................... | 606/213 |
| 6,447,524 B1 * | 9/2002 | Knodel et al. ................. | 606/151 |
| 6,537,300 B2 | 3/2003 | Girton | |
| 6,562,051 B1 * | 5/2003 | Bolduc et al. ................. | 606/143 |
| 6,572,626 B1 * | 6/2003 | Knodel et al. ................. | 606/139 |
| 6,623,508 B2 | 9/2003 | Shaw et al. | |
| 6,635,066 B2 * | 10/2003 | Tanner et al. ................. | 606/151 |

(Continued)

FOREIGN PATENT DOCUMENTS

| | | |
|---|---|---|
| DE | 196 20 620 A1 | 11/1997 |
| DE | 697 34 015 | 6/2006 |

(Continued)

OTHER PUBLICATIONS

J.B. Madigan et al., "Arterial Closure Devices," The Journal of Cardiovascular Surgery, 2007, vol. 48, pp. 607-624.

*Primary Examiner* — Julian W Woo
(74) *Attorney, Agent, or Firm* — DLA Piper LLP (US)

(57) ABSTRACT

A puncture seal that seals a hollow organ having a puncture opening in a wall includes an inner bearing element that bears on an intraluminal side of the wall of the hollow organ, and a connection element connected to the inner bearing element and which, when the seal is fitted on the wall, protrudes through the puncture opening, wherein the inner bearing element has a surface area greater than the puncture opening, the inner bearing element is a continuous strip extending in an arc shape and strip sections lie substantially flat alongside one another in a fitted state, and the strip sections have a width that is smaller than the greatest length of the puncture opening, and the inner bearing element along the strip can be inserted into the hollow organ through the puncture opening and substantially parallel to the wall of the hollow organ.

23 Claims, 5 Drawing Sheets

(56) References Cited

U.S. PATENT DOCUMENTS

| | | |
|---|---|---|
| 6,764,500 B1 | 7/2004 | Muijs Van de Moer et al. |
| 6,837,893 B2 * | 1/2005 | Miller .......................... 606/139 |
| 7,169,168 B2 | 1/2007 | Muijs Van de Moer et al. |
| 7,223,280 B2 * | 5/2007 | Anson et al. .................. 606/215 |
| 2003/0120291 A1 | 6/2003 | Chin et al. |
| 2005/0033361 A1 | 2/2005 | Galdonik et al. |
| 2005/0187564 A1 | 8/2005 | Jayaraman |
| 2006/0212047 A1 | 9/2006 | Abbott et al. |
| 2007/0135842 A1 | 6/2007 | Van de Moer et al. |

FOREIGN PATENT DOCUMENTS

| | | |
|---|---|---|
| EP | 0 474 752 B1 | 3/1992 |
| EP | 0 474 752 B2 | 3/1992 |
| EP | 0 776 179 A1 | 6/1997 |
| EP | 0 955 901 A1 | 11/1999 |
| WO | 89/11301 A1 | 11/1989 |
| WO | 98/22027 A1 | 5/1998 |

* cited by examiner

PUNCTURE SEALS FOR CLOSING HOLLOW ORGANS HAVING A PUNCTURE OPENING

RELATED APPLICATIONS

This application claims priority of German Patent Application No. 10 2008 034 534.2, filed Jul. 18, 2009, herein incorporated by reference.

TECHNICAL FIELD

This disclosure relates to puncture seals for closing hollow organs such as blood vessels having a puncture opening in a wall.

BACKGROUND

In angiology, cardiology, interventional radiology, neuroradiology, and in other fields, for example, in surgery, percutaneous transluminal catheterization procedures are performed in hollow organs. For these procedures, the common femoral artery in the inguinal region is generally used as the access route. An opened artery remains at the end of the procedure. In the artery, blood pulsates with a systolic pressure of more than 100 mmHg. If the arterial opening is not closed, there is a danger of development of a hemorrhage which, as a hematoma and/or false aneurysm, takes on clinical importance, i.e., has to be treated. The surgical access route is closed off at the end of the procedure to prevent these complications, either by compression or use of a sealing system. If the lock diameter needed for the intervention is greater than 5 Charrière, sealing systems are routinely used to seal the arterial opening. Catheterization procedures are also increasingly being performed for which large-lumen locks are needed. The diameters of these, for example, for inserting an aorto-iliac endoprosthesis, are as much as 28 Charrière.

The publication "Arterial closure devices" by J. B. Madigan, L. A. Ratnam and A. M. Belli in The Journal of Cardiovascular Surgery, 2007; 48:607-624 contains an overview of the sealing systems hitherto used in practice. Sealing systems described in that publication, and other sealing systems, are known from the following patent literature: U.S. Pat. Nos. 4,744,364, 5,350,399, 5,441,517, 5,593,422, 5,620,461, 5,916,236, 6,764,500 B1 (corresponding to EP 0 474 752 B1), U.S. Pat. No. 7,169,168 B2, US 2007/0135842 A1, WO 89/11301, EP 0 776 179 B1, DE 196 20 620 A1, EP 0 955 901 B1 and EP 0 474 752 B2.

Generally, in the known sealing systems, an inner bearing element, designed to bear on the inner face of the hollow organ in the area of the puncture opening, is inserted in a folded or rolled-up state through a catheter into the interior of the hollow organ and then deployed. The inner bearing element is generally provided with a retention element or connection element which is guided through the puncture opening in the wall of the hollow organ and through the overlying skin and is secured there to retain the bearing element at the correct location. A string or rod generally serves as the retention or connection element. Outer bearing elements are also known which are placed on the outer face of the wall of the hollow organ and are connected to the inner bearing element via the connection element.

Introduction of the inner bearing element and the deployment thereof can lead to complications, particularly if the diameter of the hollow organ is small. In some sealing systems, the cross section of flow through the hollow organ is modified in an unacceptable manner not only during fitting of the system, but also thereafter.

It could therefore be helpful to make available a sealing system in which the inner bearing element can be easily introduced into the hollow organ in a manner substantially independent of the diameter of the hollow organ and without disturbing the flow through the organ.

SUMMARY

I provide a puncture seal that seals a hollow organ having a puncture opening in a wall including an inner bearing element that bears on an intraluminal side of the wall of the hollow organ, and a connection element connected to the inner bearing element and which, when the seal is fitted on the wall, protrudes through the puncture opening, wherein the inner bearing element has a surface area greater than the puncture opening, the inner bearing element is a continuous strip extending in an arc shape and strip sections lie substantially flat alongside one another in a fitted state, and the strip sections have a width that is smaller than the greatest length of the puncture opening, and the inner bearing element along the strip can be inserted into the hollow organ through the puncture opening and substantially parallel to the wall of the hollow organ.

BRIEF DESCRIPTION OF THE DRAWINGS

Further features and advantages of my seals will become clear from the following description, of representative examples of structures and the drawings. The individual features can be implemented either singly or in combination with one another.

DETAILED DESCRIPTION

Figure 1:
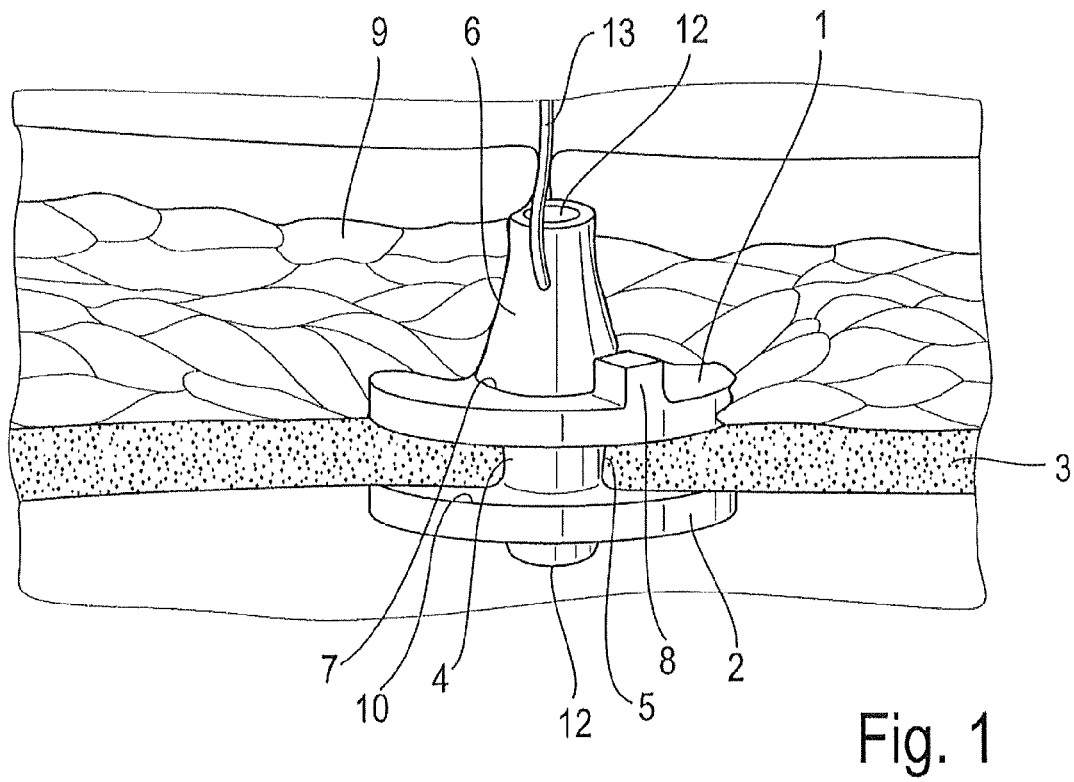
FIG. 1 shows a puncture seal in the fitted state.

It will be appreciated that the following description is intended to refer to specific examples of structure selected for illustration in the drawings and is not intended to define or limit the disclosure, other than in the appended claims.

Proceeding from the sealing system described above, I provide puncture seals wherein the inner bearing element is designed as a continuous strip extending in an arc shape, wherein strip sections lie flat alongside one another in the fitted state, and the strip sections have a width that is smaller than the greatest length of the puncture opening, and the inner bearing element can be inserted into the hollow organ in a manner substantially parallel to the wall of the hollow organ.

In an artery, which is what the hollow organ is in most cases, the puncture opening is generally not circular, but slit-shaped, and the slit in the wall of the artery generally extends transversely with respect to the longitudinal direction of the artery. This shape of the puncture opening is conditioned by the direction of the fibers in the wall of the artery. In contrast to the prior art, it is not necessary to make the inner bearing element small in terms of its surface area, i.e., to collapse it or roll it up, to be able to convey it through the puncture opening. In my case, by contrast, the normally flat bearing element is subdivided substantially linearly in such a way that the surface of the bearing element provides a continuous strip whose width is smaller than the greatest length of the puncture opening. This allows the bearing element as strip to be inserted through the slit of the puncture opening into the interior of the hollow organ, specifically in a manner substantially parallel to the wall of the hollow organ. This avoids impeding the cross section of the hollow organ and, in particular, avoids damaging the opposite inner face of the wall.

The length of the strip can be a multiple of the greatest length of the puncture opening, generally at least about 5 times, preferably at least about 10 times. The surface area of the inner bearing element is preferably greater in terms of the surface dimensions, i.e., length and width or diameter, than the width of the strip sections of the strip. Generally, the surface dimension is at least about 3 times the width of a strip, preferably about 5 times. This means that at least about three, preferably about five, strip sections lie alongside one another.

The strip may be substantially flat at least in the fitted state and extends in an arc shape in the surface of the inner bearing element. This means that the strip at least in the fitted state assumes the form that a planar inner bearing element normally has. In the state when not fitted, the strip can be curved not only in the surface, but also perpendicular thereto, as will be discussed in more detail below. The strip is preferably designed in an arc shape in such a way that adjacent strip sections are formed. This means that the strip sections preferably lie so close together that a full surface is again obtained. The inner bearing element, at least in the fitted state, preferably has a disk-shaped configuration.

The disk may be substantially circular. The strip can curve in a spiral, resulting in a substantially circular disk shape. Thus, the strip preferably has the shape of a flat spiral. The strip may also have the shape of a coil or helical spiral. This means that the planar strip is curved in a spiral and the individual windings of the spiral at the same time have a helical pitch. The strip is preferably made of an at least partially elastic material. Thus, the inner bearing element in a first functional state (prior to being fitted) may be designed as a coil and, in a second functional state (after being fitted) is plate-shaped or disk-shaped with a substantially circular bearing surface. The inner bearing element can preferably be converted from the first functional state to the second functional state by pulling the connection element.

The strip may curve in a substantially serpentine or meandering shape. In that form, the strip normally lies flat. However, it is also possible to give the strip a certain inclination out of the plane. In the fitted state, it then lies with a selected pretensioning on the vessel wall.

It is preferable that adjacent strip sections have a spacing from one another, or can be brought into such a spacing, that corresponds at least to the wall thickness of the hollow organ. This means in practice that this spacing is at least about 1 mm, generally about 1 to about 2 mm, since the wall thickness of an artery in the inguinal region is approximately 1 mm. The spacing of adjacent strip sections can lie in the surface of the inner bearing element and/or perpendicular thereto. Thus, a clear gap can be present in the surface between the strip sections. A gap can also be generated, by an inclination of the strip sections. A combination of both types is also possible. Thus, the spacing between the adjacent strip sections can be generated or widened by elastic displacement of the strip sections obliquely, preferably perpendicularly, with respect to the surface of the inner bearing element. On the other hand, by means of different inclination, adjacent strip sections can have a spacing that can be made smaller or can be eliminated by elastic compression perpendicular to the surface of the bearing element. This possibility is of particular advantage in instances in which adjacent strip sections mutually overlap in the fitted state. Increased stabilization of the strip-shaped bearing element can be achieved by such overlapping. Such overlapping can be obtained by the partition lines between the strip sections extending obliquely with respect to the surface of the inner bearing element. Mutual engagement of the strip sections at their edges is also possible. Thus, adjacent strip sections can form a substantially closed surface in the fitted state.

The connection element serves to position the inner bearing element and hold it at the correct location and create a connection from the inner bearing element to the outside of the hollow organ. It can be flexible, for example, in the form of a wire or cord. It is preferably rigid. Particularly when it is rigid, it is advantageously connected to the inner bearing element in a rotationally fixed manner. The connection element is preferably formed in one piece with the inner bearing element.

The inner bearing element may be assigned an outer abutment, in particular, an outer bearing element for bearing on the extraluminal side of the hollow organ. The abutment, in particular, the outer bearing element, is preferably fixed on the connection element. Further, the abutment, in particular, the outer bearing element, may have a central hole having an inner diameter that essentially corresponds to the outer diameter of the connection element. The inner bearing element and the outer abutment, can be connected to each other in the fitted state with the aid of the connection element. By means of the connection, it is possible, if so desired, to exert a certain bearing pressure, between inner bearing element and an abutment, on the wall that is to be sealed off.

The inner bearing element is or can be connected to a tensile strength application aid. Such an application aid can be combined with the connection element. Preferably, the application aid is provided in a tubular shape, in particular, as a rotating sleeve type. Furthermore, the application aid can in particular be flexible and can be formed by a cord or a wire, for example. The application aid can at the same time serves as connection element.

The application aid can be formed by a continuation of a substantially rigid connection element. After the puncture seal has been fitted in place, parts of the connection element that are no longer required can be shortened. It is also possible to provide separate application aids that can be brought into operative connection to the inner bearing element. They engage preferably indirectly via the connection element or via an abutment. The outer bearing element may have a central opening with an internal diameter that corresponds substantially to the external diameter of the connection element. The outer bearing element can thus be pushed onto the connection element. Locking elements can preferably be provided, by means of which the outer bearing element can be secured on the connection element.

The inner bearing element and preferably also the connection element may have a preferably closable through-opening that is designed to receive a guide wire lying in the hollow organ. Such a guide wire normally lies in the hollow organ during a surgical procedure or intervention and, in particular, within a tubular instrument, particularly a catheter or trocar, inserted into the hollow organ. After the procedure, the tubular instrument can be removed, such that only the guide wire remains in the hollow organ and protrudes therefrom. The individual parts of the sealing system can then be pushed onto the protruding part of the guide wire, the wire being used to find the puncture opening, not normally visible, for insertion of the inner bearing element. The through-opening or the through-channel formed by it is preferably closable, such that it can be closed after the seal has been fitted in place and after removal of the guide wire. The through-opening can be closed, for example, by pinching off the connection element, particularly upon shortening of the connection element for removal of a continuation thereof serving as application aid. Such a structure with a through-opening, in particular, combined with a guide wire, is preferably assigned a tubular application aid, which can likewise be pushed over the guide wire.

The connection element normally engages at the center of the strip-shaped inner bearing element and can form the center of the inner bearing element. If the inner bearing element is designed as a flat spiral, for example, then the center is the inner start of the spiral. If the inner bearing element is designed in a meandering configuration, then the center preferably lies in a middle strip section. In a spiral configuration, the inner end of the spiral is normally chosen as the start for insertion through the puncture opening. However, structures are also possible in which the outer end can be used as the start for insertion. In the case of strips that curve in a meandering configuration, one or other end can be used as the start for insertion into the hollow organ.

All parts of the sealing system are preferably made of biocompatible material. The individual parts can be resorbable or nonresorbable. If the main functional parts of the seal are not made or resorbable material, then the seal is preferably a seal that can be removed again. In contrast to the prior art, the strip-shaped inner-bearing element of the seal can be guided back out through the puncture opening in the same way as it was inserted. The puncture opening is then available again for a renewed intervention.

Parts remaining on the hollow organ after installation are preferably made to be resorbable. Preferably, all parts of the seal are made of a resorbable synthetic material. The resorption time and mechanical properties can be predetermined by choice of suitable materials. The resorption time is preferably about 6 to about 24 weeks in vivo. The resorption of the materials of the seal can proceed in parallel with the wound healing, such that the puncture opening heals as the parts of the seal are resorbed.

Suitable materials for the resorbable parts may be, in particular, synthetic polymers such as polyglycolide, polylactide, poly-ε-caprolactone, polytrimethylene carbonate and poly-p-dioxane. Copolymers from monomers of these polymers are also suitable.

As has already been mentioned, the sealing system is preferably used in angiology, cardiology, interventional radiology, neuroradiology and/or surgery, for sealing a hollow organ, in particular, a blood vessel, having a puncture opening.

Figure 2:
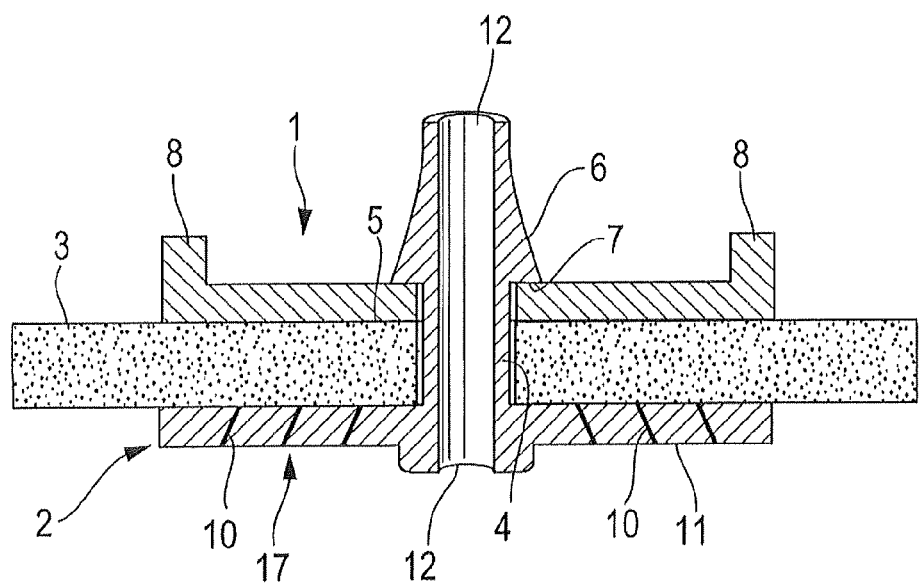
FIG. 2 shows a cross section through the seal according to FIG. 1.

Turning to FIGS. 1 and 2, a seal has what is basically a push-button design and is shown in the state when fitted for use. An outer bearing element 1 has the shape of a circular perforated disk. A second bearing element 2, serving as an abutment, also has a circular shape and has substantially the same diameter as the bearing element 1. The bearing element 1 lies on the outer face of an artery wall 3. The bearing element 2 lies on the inner face of the artery wall. The two bearing elements 1 and 2 are interconnected by, a connection element 4, which protrudes through a puncture opening 5 in the artery wall 3. The connection element 4 is tubular and connected to the inner bearing element 2 in a non-releasable manner, for example, formed in one piece with the latter. The connection element 4 extends through the outer perforated-disk-shaped bearing element 1 and, in an area protruding beyond this bearing element, has a locking element 6 by means of which the two bearing elements 1 and 2 are locked relative to each other and are held tightly on the inner side and outer side of the artery wall. The locking element 6 has a conical thickened part on the connection element 4, which thickened part is elastic and, in the area of greatest diameter, has an undercut or shoulder 7. To fix it, the bearing element 1 is pushed over the conical widening and snapped in behind the shoulder 7. On its outer face directed away from the artery wall 3, the outer bearing element 1 has two cams 8, of which only one can be seen in FIG. 1. The other is concealed by the skin or subcutaneous tissue 9 lying over the artery wall 3. The cams 8 serve for the engagement of a tool that serves as an application aid.

The outer bearing element 1 is designed as a solid perforated disk. By contrast, the inner bearing element 2 is divided by a partition line 10 extending in a spiral shape from the inside outward. In this way, the inner bearing element 2 itself is designed in a spiral shape, wherein the turns of the flat spiral are present as flat strips 11 whose width in the radial extent is smaller than the greatest lengthwise extent of the opening 5 in the artery wall 3. The spiral partition line 10 preferably extends obliquely with respect to the surface of the bearing element, and specifically outwardly in the direction oriented away from the first bearing element. There is, therefore, an overlapping of the strips 11, which leads to mutual stabilization in the state of use.

The through-opening 12 in the tubular connection element 4 is closed for sealing purposes. A thread 13, which is secured to the tubular connection element, particularly in the conical area, can be provided to pull the tubular connection element 4 through the opening of the outer bearing element 1 designed as perforated disk.

Figure 3:
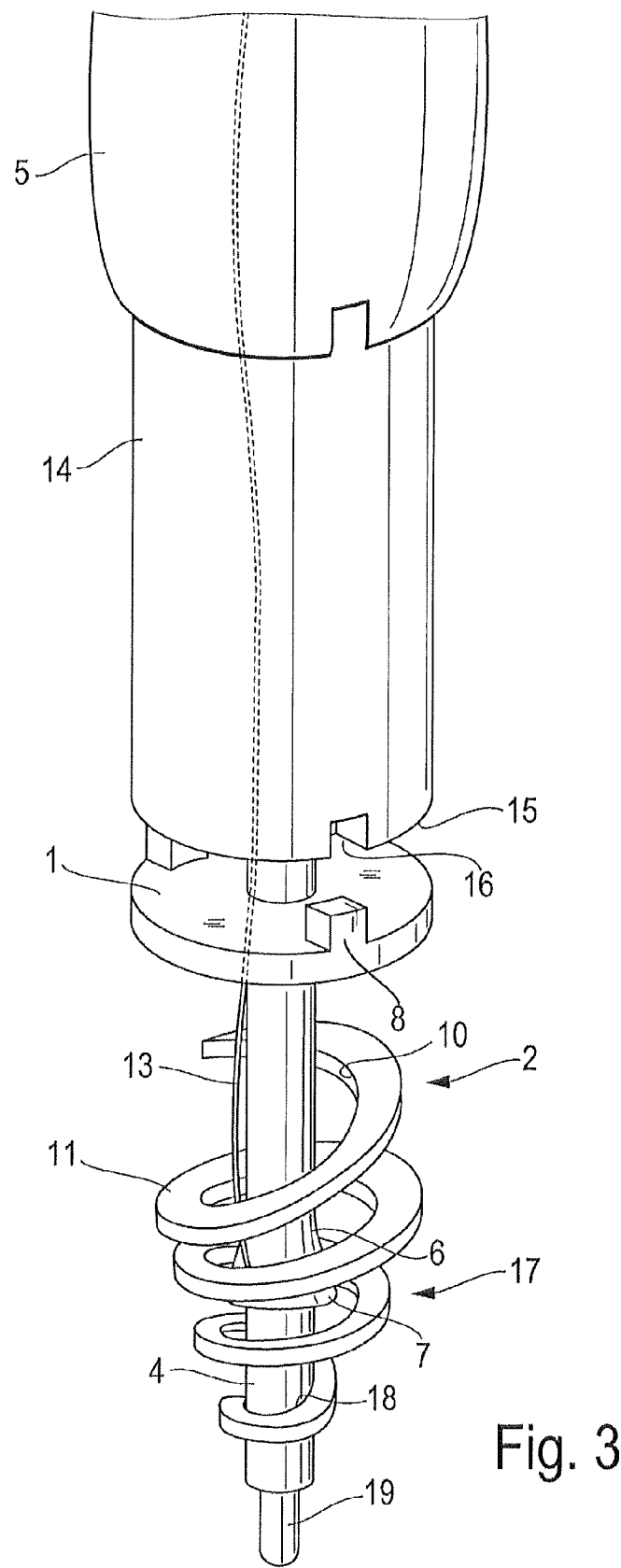
FIG. 3 shows the seal of FIGS. 1 and 2 in the not yet fitted state.

FIG. 3 shows a sealing system in the form of the elements of the seal according to FIGS. 1 and 2 and a tool 14. This tool is tubular and, at its end face 15, has two recesses 16 into which the cams 8 of the outer bearing element 1 fit. The outer bearing element 1 is displaceable, in the axial direction on the tubular connection element 4, but in one example is connected thereto in a rotationally fixed manner. In that example, the connection element 4 is longer before and during assembly than it is after assembly, at which time it is present in a shortened form. For this purpose, the connection element 4 can be provided with a longitudinal groove into which a radially inwardly directed projection (not shown) of the first connection element protrudes. By turning the rotary tool 14, a rotation movement can thus be imparted to the elements of the seal.

FIG. 3 shows the spiral-shaped inner bearing element 2 in the tensioned state. It has the form of a coil 17 in which the individual turns are mutually offset both in the axial direction and also in the radial direction. The spiral is furthermore designed as a flat spiral, i.e., the individual strip-shaped windings, in the state when pressed together, lie flat alongside each other to form the disk-shaped inner bearing element. As has already been mentioned above, the inner bearing element 2 is connected in one piece to the connection element 4, for example, being produced together with the latter by injection molding. However, the connection 18 is preferably unstable, such that the individual windings of the coil 17 can be applied when required onto the tubular connection element 4. In this way, the maximum thickness of the seal, upon insertion through the opening 5 in the artery wall 3, corresponds to the sum of the width of the strip 11 and the diameter of the connection element 4, which is substantially less than the diameter of the whole bearing element 2. FIG. 3 also shows a flexible guide wire 19, which is guided through the opening 12 in the connection element 4 and through the tool 14. Such a guide wire normally lies in the artery during a percutaneous transluminal catheterization procedure. It is possible to leave the guide wire in the artery after the procedure and to use it as a guide for centering the seal, by means of the tubular connection element 4 being pushed over the wire 19 and thus automatically guided to the opening 5 in the artery, which opening is normally covered by the cutaneous tissue or subcutaneous tissue 9 and is not particularly easy to find.

Figure 4:
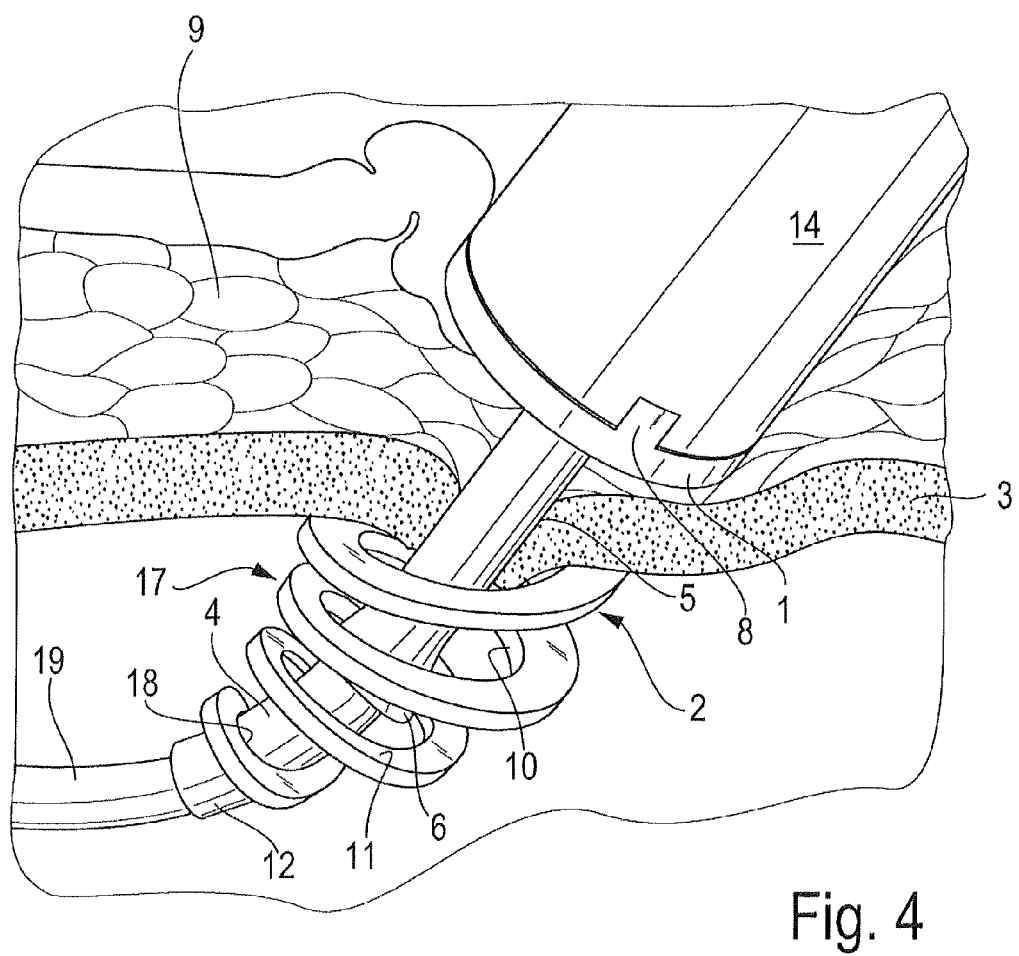
FIG. 4 shows the seal according to FIGS. 1 to 3 during fitting.

FIG. 4 shows the seal being applied to an artery wall. The seal components are introduced into the artery obliquely since, on the one hand, the guide wire 19 extends obliquely through the artery wall 3 and continues obliquely within the artery and, on the other hand, oblique insertion leaves more space in the artery. The insertion is effected by rotary movement of the tool 14, as a result of which the coil 17 is screwed in through the wall of the artery. As soon as the coil has been guided completely through the artery wall 3, the connection element 4 is pulled through the opening in the outer bearing element, with the coil 17 at the same time being compressed to form the disk-shaped inner bearing element 2. This can be done directly by pulling on the elongated connection element 4 or by palling on the thread 13. When the thickened part or locking element 6 of the connection element 4 is guided through the opening of the outer bearing element 1 and the locking connection snaps into place, then the state shown in FIG. 1 is reached, in which the two bearing elements 1 and 2 bear on the artery wall 3 resiliently and sealingly by virtue of the spring action of the coil 17. After the guide wire 19 has been withdrawn, the excess part of the connection element 4, as shown in FIGS. 3 and 4, can be cut off and at the same time pinched so as to provide a tight seal.

The individual parts of the seal are preferably made of resorbable synthetic materials such as polymers and copolymers of α-hydroxylic acids and the like, such as glycolide, lactide, trimethylene carbonate and caprolactone. The desired resorption time can be set by suitable choice of the polymers. This is preferably chosen such that the resorption of the seal proceeds at the same rate as the closing of the opening in the artery wall.

Figure 5:
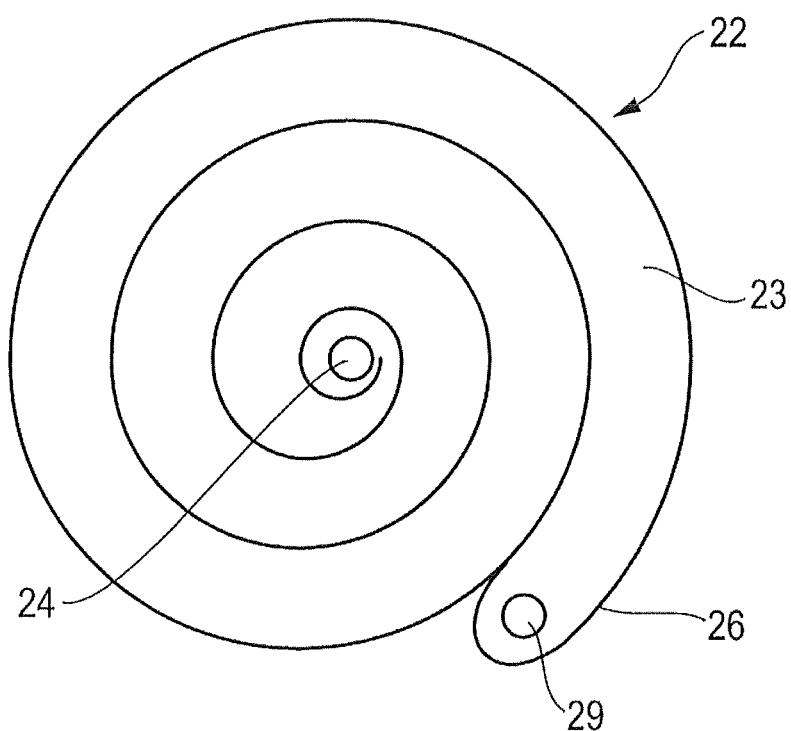
FIG. 5 shows another seal in a plan view.
Figure 6:
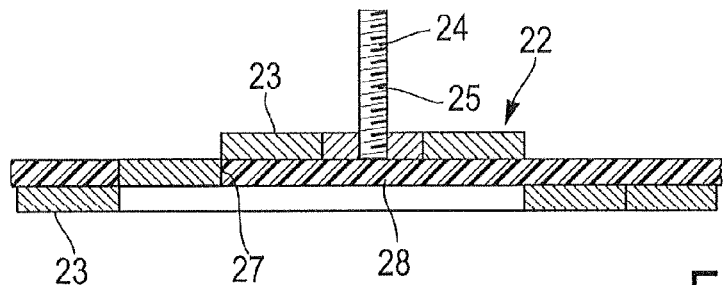
FIG. 6 shows a cross section through the seal according to FIG. 5 during fitting.
Figure 7:
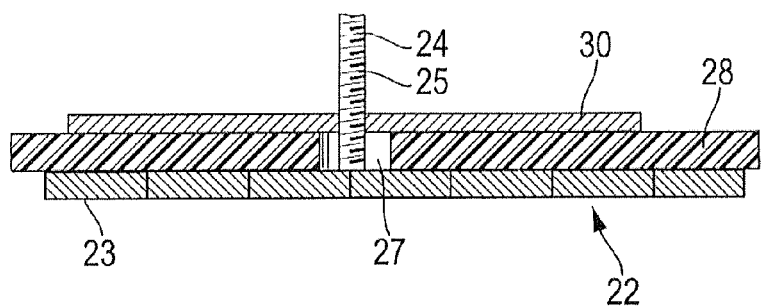
FIG. 7 shows a cross section through the seal according to FIG. 5 after fitting.

In the seal according to FIGS. 5 to 7, the drawing is made simpler by showing only an inner bearing element 22, designed as a spiral 23, and a rod-shaped connection element 24 connected thereto. The connection element 24 engages in the center of the spiral 23 and is solid. It can be provided above the spiral with a thread 25. In that seal, the free end 26 of the spiral 23 may be inserted first through a puncture opening 27 in a vessel wall 28. By turning the spiral 23, the entire spiral, from the outside inward, is then guided through the opening. The spiral 23 can be turned with the aid of the rod-shaped connection piece 24. Here too, the inner bearing element is inserted into the blood vessel in a manner substantially parallel to the vessel wall, as is shown schematically in FIG. 6. That seal is primarily suitable for use in puncture openings that are visible or can be made visible by auxiliary means. The free end 26 can then be inserted directly into the opening 27 in the vessel wall. If the opening 27 is not visible, it is again possible to provide a guide wire, which protrudes through the opening 27 in the vessel wall. The free end 26 of the spiral 23 can be provided with a corresponding guide hole 29 through which the guide wire is guided. The opening 27 in the vessel wall 28 is therefore found with the aid of the guide wire. After insertion of the free end 26, the guide wire can be removed and the rest of the spiral 23 can be introduced by turning. In that seal, the outer bearing element can be a perforated disk 30 which has an inner thread and which is pushed over the rod-shaped connection element 24 and, by rotation on the thread 25, can be turned until it bears on the outer wall of the vessel (FIG. 7).

Figure 8:
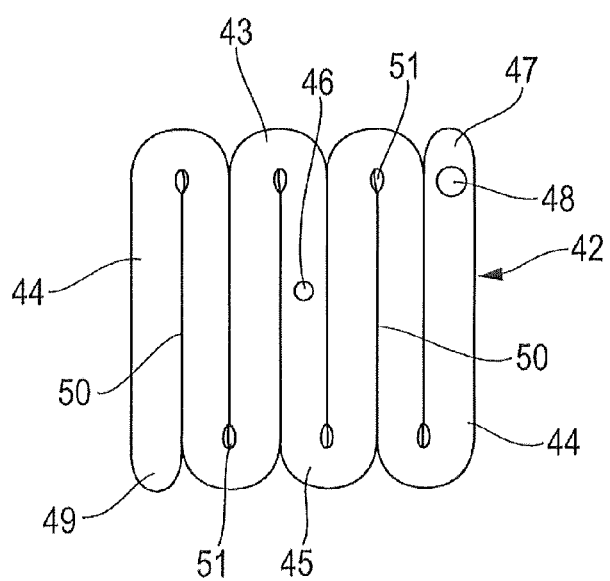
FIG. 8 shows a further seal.

In the seal according to FIG. 8, an inner bearing element 42 is provided which is once again strip-shaped, but this time in the form of a flat meandering portion 43 with strip sections bearing on one another. The strip sections 44 are provided in an odd number. In this case, there are seven. Located at the center of the middle strip section 45 is the point of engagement for a connection element 46, which in this case is designed as a flexible thread or wire. In this seal, insertion of the inner bearing element 42 through an opening in a vessel wall begins at a free end 47. Here too, the free end can be provided with a guide opening 48 through which a guide wire can be guided. After insertion of the free end 47 into the opening of the vessel, the guide wire is removed and the meander-shaped bearing element 42 is pushed section by section through the opening in the vessel wall until the other free end 49 of the meander has disappeared in the vessel. The strip sections 44 and 45 are separated from one another by narrow cuts 50. Only at the ends of the partition lines are there narrow apertures 51 to facilitate the insertion of the strip through the puncture opening.

By pulling the flexible connection element 46, the inner bearing element 42 is centered. It can then be secured by applying an outer bearing element, or by other suitable measures.

Although the apparatus has been described in connection with specific forms thereof, it will be appreciated that a wide variety of equivalents may be substituted for the specified elements described herein without departing from the spirit and scope of this disclosure as described in the appended claims.

The invention claimed is:

1. A puncture seal that seals a hollow organ having a puncture opening in a wall comprising:
    an inner bearing element configured to bear on an intraluminal side of the wall of the hollow organ, and
    a connection element connected to the inner bearing element and which, when the seal is fitted on the wall, is adapted to protrude through the puncture opening, wherein the inner bearing element has a surface area configured to be greater than the area of the puncture opening, at the wall the inner bearing element is a continuous strip extending in an arc shape and comprising separable strip sections which lie flat alongside one another and form a closed surface in a fitted state, and the strip sections are configured to have a width that is smaller than the greatest length of the puncture opening, and the continuous strip is configured to be inserted into the hollow organ through the puncture opening and form the closed surface substantially parallel to the wall of the hollow organ.

2. The puncture seal as claimed in claim 1, wherein the length of the strip is adapted to be a multiple of the greatest length of the puncture opening.

3. The puncture seal as claimed in claim 1, wherein a surface area of the inner bearing element is greater in the surface dimensions than the width of the strip sections of the strip.

4. The puncture seal as claimed in claim 1, wherein the strip, at least in the fitted state, is substantially flat and is extendable in an arc shape to define a surface of the inner bearing element.

5. The puncture seal as claimed in claim 1, wherein the strip is configured in an arc shape in such a way that adjacent strip sections form.

6. The puncture seal as claimed in claim 1, wherein the inner bearing element, at least in the fitted state, has a disk-shaped configuration.

7. The puncture seal as claimed in claim 1, wherein the strip curves in a spiral shape.

8. The puncture seal as claimed in claim 1, wherein the strip is in the form of a flat spiral.

9. The puncture seal as claimed in claim 1, wherein the strip is a helical coil.

10. The puncture seal as claimed in claim 1, wherein the strip curves in a substantially serpentine or meandering shape.

11. The puncture seal as claimed in claim 1, wherein adjacent strip sections have a spacing, or can be brought into a spacing, that substantially corresponds at least to the wall thickness of the hollow organ.

12. The puncture seal as claimed in claim 1, wherein a spacing between adjacent strip sections can be generated or widened by elastic displacement of the strip sections obliquely with respect to the surface of the inner bearing element.

13. The puncture seal as claimed in claim 1, wherein adjacent strip sections have a spacing that can be made smaller or eliminated by elastic compression.

14. The puncture seal as claimed in claim 1, wherein adjacent strip sections mutually overlap in the fitted state.

15. The puncture seal as claimed in claim 1, wherein adjacent strip sections form a substantially closed surface in the fitted state.

16. The puncture seal as claimed in claim 1, wherein the connection element is formed in one piece with the inner bearing element.

17. The puncture seal as claimed in claim 1, wherein the inner bearing element has an outer abutment that is configured to bear on an extraluminal side of the hollow organ.

18. The puncture seal as claimed in claim 17, wherein the abutment can be secured on the connection element.

19. The puncture seal as claimed in claim 17, wherein the abutment has a central opening with an internal diameter that corresponds substantially to an external diameter of the connection element.

20. The puncture seal as claimed in claim 1, wherein the inner bearing element and the connection element have a closable through-opening that receives a guide element adapted to lie in the hollow organ.

21. The puncture seal as claimed in claim 1, wherein the inner bearing element has an application aid which is or can be connected tautly to the inner bearing element.

22. The puncture seal as claimed in claim 21, wherein the application aid has a tubular configuration.

23. The puncture seal as claimed in claim 1, wherein all parts of the seal are resorbable within a period of 6 to 24 weeks.

* * * * *